United States Patent [19]

Taylor

[11] 4,111,837
[45] Sep. 5, 1978

[54] HOMOLOGATION OF ALKANOLS

[75] Inventor: Paul D. Taylor, Clinton, N.J.

[73] Assignee: Celanese Corporation, New York, N.Y.

[21] Appl. No.: 814,977

[22] Filed: Jul. 12, 1977

Related U.S. Application Data

[62] Division of Ser. No. 718,695, Aug. 30, 1976.

[51] Int. Cl.² .............................................. B01J 31/28
[52] U.S. Cl. .................................. 252/430; 252/443; 568/902
[58] Field of Search ........... 260/642 R, 642 B, 642 C; 252/443, 430

[56] References Cited

U.S. PATENT DOCUMENTS

| | | | |
|---|---|---|---|
| 2,623,906 | 12/1952 | Gresham | 252/443 X |
| 2,691,046 | 10/1954 | Hasek | 252/443 X |
| 3,957,684 | 5/1976 | Strohmeyer et al. | 252/443 X |

*Primary Examiner*—Patrick P. Garvin
*Attorney, Agent, or Firm*—George Depaoli; Kenneth A. Genoni

[57] ABSTRACT

This invention provides an improved process for converting methanol into ethanol and ethanol precursors with higher efficiency than prior art methods. This invention further provides a novel heterogeneous co-catalyst system adapted for alkanol homologation which consists essentially of cobalt carbonyl and rhenium metal.

3 Claims, No Drawings

HOMOLOGATION OF ALKANOLS

This is a division, of application Ser. No. 718,695, filed Aug. 30, 1976.

BACKGROUND OF THE INVENTION

Earliest research on carbon monoxide/hydrogen chemistry dates back to 1902 when Sabatier and Senderens passed CO and $H_2$ (1:3) over reduced nickel at 1 atm and produced methane. It was reported by BASF in 1913 that at higher pressures (100–200 atm) and temperatures (300°–400° C) the major products are liquids. Later in 1923 Fischer and Tropsch disclosed the use of alkalized iron turnings as catalysts for the production of an oily liquid from CO and $H_2$ at 100–150 atm and 400°–425° C. This product contained mainly oxygenated compounds such as alcohols, acids, aldehydes, ketones and esters, and a very small quantity of hydrocarbons.

Continuing research with Fischer-Tropsch catalysts has lead to the development of commercial scale plants for methanol synthesis from carbon monoxide and hydrogen.

In 1949 Wender et al (J.A.C.S., 71, 4160) reported the homologation of alcohols by reaction with synthesis gas in the presence of a cobalt catalyst under oxo reaction conditions. There is described the conversion of t-butyl alcohol into isoamyl alcohol, and the conversion of benzyl alcohol into $\beta$-phenylethyl alcohol. In 1951 these workers reported the conversion of methanol into ethanol under oxo reaction conditions with a cobalt catalyst. Other products of the reaction included methyl formate, methyl acetate, ethyl acetate, acetaldehyde, propyl alcohol, butyl alcohol and methane.

U.S. Pat. No. 2,623,906 discloses that at pressures above 1,000 atmospheres, in the presence of a cobalt catalyst, primary, secondary and tertiary alcohols react with synthesis gas to form glycol ethers, and monohydric alcohols containing at least one more carbon atoms per molecule than the original alcohol reactant.

U.S. Pat. No. 3,285,948 discloses that an improved yield of ethanol from methanol can be obtained by conducting the synthesis gas homologation reaction in the presence of a cobalt catalyst which is promoted with iodine and a metal halide selected from ruthenium halide and osmium halide.

The prior art processes for homologation of alkanols are generally uneconomical because of the low selectivity of the catalyst systems and the concomitant large quantities of aldehydes, esters, acids and hydrocarbons which are produced and which are difficult to separate into individual components.

Accordingly, it is an object of this invention to provide an improved process for homologation of alkanols with carbon monoxide and hydrogen.

It is another object of this invention to provide a novel heterogeneous co-catalyst adapted for high efficiency conversion of methanol to ethanol and ethanol precursors.

It is a further object of this invention to provide a process for preparing an improved cobalt catalyst system for liquid phase homologation of alkanols.

Other objects and advantages of this invention shall become apparent from the following description and exemplary data.

DESCRIPTION OF THE INVENTION

One or more object of the present invention are accomplished by the provision of an improved homologation process for producing ethanol which comprises reacting methanol in liquid phase with carbon monoxide and hydrogen at a temperature in the range between about 100° C and 350° C and a pressure in the range between about 1,000 and 15,000 psi in the presence of a heterogeneous co-catalyst consisting essentially of a methanol-soluble cobalt derivative and a methanol-insoluble rhenium derivative.

The invention process has general applicability for the homologation of alkanols, substituted alkanols, alkane polyols, and the like. The order of reactivity of the alkanols under the process conditions is tertiary $>$ secondary $>$ primary, with the exception that methanol reacts with synthesis gas more rapidly than secondary alkanols. Homologation of alkanols and alkanediols having between 1 and about 12 carbon atoms (e.g., methanol, decanol and ethylene glycol) and substituted alkanols (e.g., benzyl alcohol) is readily accomplished by the invention process.

PROCESS CONDITIONS

The alkanol being reacted with synthesis gas provides the liquid phase reaction medium for the process. If desired, an alkanol-miscible diluent such as dioxane, tetrahydrofuran, and the like, may be included to moderate the rate of reaction and the exothermic heat of reaction.

Illustrative of a typical procedure, methanol is charged to an autoclave reactor, and then there is introduced a heterogeneous co-catalyst system of methanol-soluble cobalt derivative and methanol-insoluble rhenium derivative as is more fully described hereinbelow.

The reactor is pressurized with a gas mixture of carbon monoxide and hydrogen. Synthesis gas produced by the reaction of carbonaceous material with water is suitable. Mixtures of carbon dioxide and hydrogen, carbon dioxide and carbon monoxide and hydrogen, carbon monoxide and water, and the like, may also be employed. Whether introduced originally, or produced in situ under processing conditions, the reaction elements of carbon monoxide and hydrogen are required.

The relative molar quantities of carbon monoxide and hydrogen present during the alkanol homologation reaction can vary in the range between about 10:1 and 1:10, and preferably in the range between about 3:1 and 1:3. An inert diluent gas such as nitrogen or helium may be included if desired.

The homologation reaction requires a relatively high pressure for optimum selectivity and yield of homologation product. The pressure is maintained in the range between about 1,000 and 15,000 psi, and preferably in the range between about 2,000 and 10,000 psi.

The homologation reaction is conducted at a temperature in the range between about 100° C and 350° C, and preferably in the range between about 110° C and 250° C. The preferred temperature range for homologation of methanol to ethanol is between about 160° C and 200° C.

The reaction period which is optimum for a particular alkanol will vary, depending on the pressure and temperature and $CO:H_2$ molar ratio. Nominally, the reaction period can vary in the range between about 2 minutes and 4 hours. In a typical operation the optimum reaction period will be in the range between about 0.1 and 2 hours. A suitable reaction period for methanol homologation is between about 0.1 and 1 hour at 160°–200° C and 2,000–4,000 psi.

The invention process can be conducted either continuously or batchwise. In a continuous process, a high pressure separator can be employed to remove the reaction products from the reactor effluent stream, and the unreacted synthesis gas can be recycled.

The product mixture recovered from methanol homologation consists of ethanol and 1,1-dimethoxyethane as the principle constituents, and minor quantities of dimethyl ether and methyl acetate. If desired, 1,1-dimethoxyethane can be recycled since it is convertible into ethanol under the processing conditions. Methyl acetate can also be recycled to produce ethanol under the invention process conditions.

CATALYST PREPARATION

In another embodiment, the present invention provides a novel heterogeneous co-catalyst system having superior reactivity for highly selective conversion of an alkanol to its corresponding homolog containing an additional carbon atom. This invention further provides a method of catalyst preparation, in which critical procedures must be respected in order to achieve a novel catalyst composition which is superior to prior art catalysts for alkanol homologation reactions.

The present invention co-catalyst system consists essentially of an alkanol solution of cobalt carbonyl in contact with solid-phase rhenium metal. The rhenium functions as a hydrogenation catalyst.

Rhenium metal was found to be unique in the ability to increase the efficiency of homologation of methanol to ethanol. Hence, catalyst systems containing metals other than rhenium are ineffective for enhancing cobalt promoted homologation of methanol. Such metals include copper, chromium, zinc, palladium, rhodium, and the like.

The cobalt can be introduced into the catalyst system in any derivative form which is soluble in the alkanol medium. Suitable cobalt derivatives include salts of carboxylic acids such as cobalt acetate, cobalt propionate, cobalt naphthenate, and the like. Under the homologation reaction conditions, the solubilized cobalt derivative is converted into cobalt carbonyl and hydrocarbonyl which are the catalytically active forms of cobalt. Cobalt can also be introduced into the catalyst system directly in the form of cobalt carbonyl. This derivative can be prepared by contacting cobalt carbonate with synthesis gas at elevated temperature and pressure.

It is a critical aspect of the catalyst system that the cobalt carbonyl does not have prolonged contact with the rhenium metal in the absence of carbon monoxide. Lack of precaution results in decomposition and deactivation of the cobalt carbonyl.

In one procedure for preparing a stable highly-reactive catalyst system, a rhenium compound such as rhenium oxide or rhenium halide is admixed with an alkanol of choice and reduced with hydrogen. The finely divided rhenium metal is allowed to settle, and the reactor is flushed with carbon monoxide. Then cobalt carbonyl is introduced into the alkanol medium, and the reactor is pressurized with carbon monoxide or synthesis gas.

In another procedure, soluble derivatives of cobalt and rhenium can be dissolved in the alkanol medium. Under alkanol homologation conditions, the cobalt derivative is converted into soluble cobalt carbonyl, and the rhenium derivative is reduced to rhenium metal which precipitates as a finely divided solid. Lower oxides of rhenium can also be methanol-insoluble, e.g., $Re_2O_3$, $ReO_2$, $ReO_3$, and the like.

A convenient and advantageous method of introducing the rhenium metal into the catalyst system is as a composite with a carrier substrate. The rhenium content of the composite can vary in the range between about 0.01 and 50 weight percent, and preferably in the range between about 0.1 and 10 weight percent. Suitable carrier substrates include carbon, pumice, silica, alumina, magnesia, titania, and the like. The rhenium-composite catalyst can be prepared by conventional methods.

Alternatively, the rhenium-composite catalyst can be formed into granules or pellets and charged to a fixed bed as an integrated unit in a continuous alkanol homologation process.

In the heterogeneous co-catalyst system of the present invention, the atomic ratio of cobalt to rhenium can vary in the range between about 0.1 and 50 to 1, and preferably in the range between about 0.5 and 15 to 1.

The quantity of cobalt carbonyl catalyst employed in the homologation process can vary between about 0.001 and 20 weight percent, calculated on the weight basis of cobalt and alkanol present.

The following exemplary procedures are illustrative of specific embodiments of the present invention. As it is apparent to those skilled in the art, in the light of the foregoing disclosure numerous modifications are possible in the practice of this invention without departing from the concept or scope thereof.

EXAMPLE

A series of methanol homologation reactions were conducted in a 300 milliliter "magnadrive" stainless steel autoclave. The respective catalysts employed, and the yields of products obtained, are listed in Table I.

As a general procedure, the reactants were charged to the autoclave, which was then flushed with carbon monoxide, pressurized to 3,000 psig with $CO:H_2$ (1:1), and then heated with stirring to the reaction temperature.

Gas absorption usually commenced when the autoclave conditions reached 180°–185° C and 4000 psig. The contents of the reactor were analyzed by gas chromatography.

In most runs, the hydrogenation catalyst and 100 grams of methanol were charged to the autoclave first, then one gram of $Co_2(CO)_8$ was added. The autoclave was pressurized to 4,000 psig with $CO:H_2$ (1:1) and heated to 185°–190° C. The reaction was continued until the pressure decreased to 3,000 psig.

In Run No. 2, the rhenium metal was supported on a carbon substrate.

In Run No. 3, $Re_2O_7$ was dissolved in the methanol, pressurized to 1,800 psig with hydrogen, heated to 118° C for 2 hours, and then cooled to room temperature before the $Co_2(CO)_8$ co-catalyst was added.

As demonstrated by the data in Table I, the highest conversion of methanol to ethanol was achieved with a heterogeneous co-catalyst of methanol-soluble cobalt carbonyl and methanol-insoluble rhenium metal.

TABLE I

Methanol Homologation Catalyzed By $Co_2(CO)_8$ And A Hydrogenation Catalyst

| Run No. | Catalyst $Co_2(CO)_8$ + | Methyl Ether | Acet- aldehyde | Dimethoxy Ethane | Methyl Acetate | Ethanol | Methanol Conversion |
|---|---|---|---|---|---|---|---|
| 1 | $Co_2(CO)_8$ | 12.9 | 2.6 | 42.0 | 8.4 | 19.5 | 20.4 |
| 2 | Re/C 5% (1.0 g) | 7.0 | 1.9 | 33.0 | 12.1 | 28.9 | 26.4 |
| 3 | Re (1.0 g) $Re_2O_7$ | 6.2 | 0.0 | 16.3 | 1.6 | 48.8 | 18.9 |
| 4 | Cu $CrO_x$ (1.0 g) | 25.7 | 1.4 | 21.5 | 3.0 | 23.1 | 19.5 |
| 5 | Pd/C 10% (0.5 g) | 6.0 | 1.6 | 26.3 | 7.8 | 21.0 | 34.0 |
| 6 | Rh/C 5% (0.5 g) | exothermic reaction — uncontrolled ||||||
| 7 | Zn $CrO_x$ (1.0 g) | 11.0 | — | 38.0 | 2.0 | 19.0 | 20.0 |

What is claimed is:

1. A heterogeneous co-catalyst adapted for homologation of alkanol with hydrogen and carbon monoxide which consists essentially of an alkanol solution of cobalt carbonyl in contact with surface-active rhenium metal, wherein the cobalt carbonyl is present in a quantity between about 0.001 and 20 weight percent, based on the weight of cobalt and alkanol, and the cobalt and rhenium are provided in an atomic ratio in the range between about 0.1 and 50 to 1 of cobalt to rhenium.

2. A heterogeneous co-catalyst in accordance with claim 1 wherein the cobalt and rhenium are provided in an atomic ratio in the range of between about 0.5 and 15 to 1 of cobalt to rhenium.

3. A heterogeneous co-catalyst in accordance with claim 1 wherein the rhenium metal is supported on a carrier substrate.

* * * * *